United States Patent
Pinkos et al.

(10) Patent No.: US 6,329,532 B1
(45) Date of Patent: Dec. 11, 2001

(54) METHOD FOR SEPARATING MALEIC ANHYDRIDE FROM MALEIC ANHYDRIDE-CONTAINING MIXTURES BY STRIPPING

(75) Inventors: Rolf Pinkos, Bad Dürkheim; Ralf-Thomas Rahn, Mannheim, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/622,172

(22) PCT Filed: Feb. 11, 1999

(86) PCT No.: PCT/EP99/00900

§ 371 Date: Aug. 14, 2000

§ 102(e) Date: Aug. 14, 2000

(87) PCT Pub. No.: WO99/41223

PCT Pub. Date: Aug. 19, 1999

(30) Foreign Application Priority Data

Feb. 13, 1998 (DE) .............................................. 198 06 038

(51) Int. Cl.$^7$ ................................................. C07D 307/36
(52) U.S. Cl. ........................................... 549/262; 560/190

(58) Field of Search ............................... 562/898; 549/262

(56) References Cited

U.S. PATENT DOCUMENTS

| | | | |
|---|---|---|---|
| 4,361,710 | * | 11/1982 | Weitz et al. . |
| 4,562,283 | * | 12/1985 | Schnabel et al. . |
| 5,585,502 | * | 12/1996 | Ruggieri . |
| 6,077,964 | * | 6/2000 | Tuck . |

* cited by examiner

Primary Examiner—Paul J. Killos
Assistant Examiner—John Npo Calve
(74) Attorney, Agent, or Firm—Keil & Weinkauf

(57) ABSTRACT

The invention relates to a process for the separation of maleic anhydride from the maleic anhydride-containing reactor offgases from the preparation of maleic anhydride by the oxidation of hydrocarbons, in which this gas stream is brought into contact with a high-boiling, inert absorbent for maleic anhydride and maleic anhydride is separated from the resultant liquid absorbate phase by vapor stripping, where the stripping agent used is an alcohol, and at least some of the maleic anhydride is reacted with the alcohol to give the ester.

8 Claims, No Drawings

METHOD FOR SEPARATING MALEIC ANHYDRIDE FROM MALEIC ANHYDRIDE-CONTAINING MIXTURES BY STRIPPING

The present invention relates to a process for the separation of maleic anhydride from a gas stream containing maleic anhydride, to a process for the preparation of maleic esters, and to a process for the preparation of hydrogenation products of maleic acid derivatives which include the separation of maleic anhydride from a gas stream containing maleic anhydride.

Maleic anhydride is produced on a industrial scale by catalytic oxidation of hydrocarbons, such as benzene, butenes or butane, using air. Besides maleic anhydride, the resultant gaseous reaction mixture contains principally water, carbon monoxide and carbon dioxide.

Maleic anhydride is usually washed out of maleic anhydride-containing reactor offgases from the oxidation of hydrocarbons by quenching with high-boiling aliphatic alcohols. A process of this type is described, for example, in DE-A-31 06 819. This process has the disadvantage that, in the quenching process, some of the alcohol is lost with the offgas. These losses cause high costs.

The maleic anhydride obtainable from the reactor offgases from the oxidation of hydrocarbons and the maleic acid derivatives, such as maleic esters, obtained from maleic anhydride by reaction with liquid absorbents are frequently subjected to subsequent hydrogenation to butanediol, tetrahydrofuran or γ-butyrolactone. WO 97/43234 describes a process for the preparation of γ-butyrolactone, butane-1,4-diol and tetrahydrofuran in which maleic anhydride is washed out of the maleic anhydride-containing reactor offgases from the oxidation of hydrocarbons using a high-boiling, inert, organic solvent as absorbent, and maleic anhydride is separated from the resultant absorption product by stripping using a stream of hydrogen gas. The stripped-out maleic anhydride is then passed to a gas-phase hydrogenation for the preparation of butanediol, tetrahydrofuran and γ-butyrolactone. This process has the disadvantage of the formation of free maleic acid or fumaric acid. In the presence of even small amounts of water, as are frequently present in the reactor offgases from the oxidation of hydrocarbons, maleic anhydride forms free maleic acid, which is corrosive. Furthermore, free maleic acid tends to isomerize into fumaric acid, which has only low solubility and can cause considerable problems in the subsequent hydrogenation step due to deposition on the hydrogenation catalyst. Furthermore, maleic or fumaric acid forms succinic acid in the hydrogenation step. This has extremely low volatility, which can sooner or later result in caking of the catalyst.

It is an object of the present invention to provide a process for the separation of maleic anhydride from maleic anhydride-containing reactor offgases from the oxidation of hydrocarbons which is suitable for the preparation of maleic acid derivatives or hydrogenation products thereof and avoids the abovementioned disadvantages.

We have found that this object is achieved by a process for the separation of maleic anhydride from a maleic anhydride-containing gas stream in which the maleic anhydride-containing gas stream is brought into contact with a liquid absorbent phase containing at least one high-boiling, inert absorbent for maleic anhydride, and maleic anhydride is separated from the resultant liquid absorbate phase by vapor stripping, wherein the stripping agent used is an alcohol, at least some of the maleic anhydride reacting with the alcohol.

For the purposes of the present invention, the term absorbent phase is taken to mean the liquid mixture of absorbents. The absorbate phase is the absorbent phase loaded with the absorptive, here maleic anhydride or reaction products thereof.

In the presence of alcohol as stripping agent, at least partial alcoholysis of the maleic anhydride takes place with formation of the monoester, and in addition further esterification takes place with formation of the diester. The hydrolysis of the anhydride to free maleic acid is thus suppressed by traces of water absorbed from the gas stream in favor of ester formation. Any maleic acid formed by hydrolysis then reacts to give maleic monoesters or diesters. The proportion of free acid in the absorbate phase is consequently low.

The liquid absorbent or absorbate phase contains at least one high-boiling, inert absorbent for maleic anhydride. The inert, high-boiling absorbent generally has a boiling point which is at least 30° C., preferably at least 50° C., particularly preferably at least 70° C., higher than the boiling point of maleic anhydride.

Suitable absorbents are described, for example, in WO 97/43234. Examples are high-boiling esters of phthalic acid, terephthalic acid or maleic acid, such as dimethyl, diethyl or dibutyl phthalates, dimethyl terephthalate or dibutyl maleate, aromatic hydrocarbons, such as dibenzylbenzene, esters of cycloaliphatic acids, such as dibutyl hexahydrophthalate, furthermore polymethylbenzophenones, ethylene glycol ethers and polysiloxane ethers. Preferred absorbents are esters of aromatic and cycloaliphatic dicarboxylic acids, particularly preferably esters of phthalic acid and terephthalic acid. The high-boiling absorbent is generally present in excess in the absorbate phase. The weight ratio between the absorbent and maleic anhydride is generally from 1:1 to 100:1, preferably from 2:1 to 100:1, particularly preferably from 4:1 to 100:1.

Maleic anhydride is separated from the absorbate phase by vapor stripping using an alcohol as stripping agent. The term stripping is taken to mean the removal of the absorptive present in the absorbate phase with the aid of a desorption aid (stripping agent), with the absorptive accumulating in the stripping agent. The concentration of the absorptive in the absorbate phase is correspondingly reduced, and the absorbate phase is regenerated in the process. In addition to mass transfer from the absorbate phase, the present process also includes at least partial reaction of the absorptive with the stripping agent.

Suitable stripping agents for the novel process are in principle all alcohols which are volatile under the process conditions (stripping alcohols). Preference is given to methanol, ethanol, n-propanol, isopropanol, n-butanol, isobutanol, sec-butanol, n-pentanol and isopentanol, particularly preferably methanol, ethanol and n-butanol. The molar ratio between alcohol and maleic anhydride is generally from 1:1 to 300:1, preferably from 1.5 to 200:1, particularly preferably from 3:1 to 50:1.

The stripping is generally carried out in countercurrent, in which the maleic anhydride-loaded absorbate phase moves in the opposite direction to the stripping agent in vapor form, with intensive mass and heat exchange taking place between the falling, liquid absorbate phase and the rising vapor phase. The liquid absorbate phase is gradually depleted in maleic anhydride, while the vapor phase is correspondingly enriched in maleic anhydride or reaction products thereof. The stripping is preferably carried out in countercurrent in a column, preferably a packed column or bubble-cap column. The alcohol used as stripping agent is preferably introduced into the lower section of the column, and the maleic anhydride-loaded absorbate phase is preferably introduced into the upper section of the column. The maleic anhydride-depleted absorbate phase is obtained at the bottom of the column, and the alcohol employed as stripping agent together with the maleic acid derivatives are obtained at the head of the column.

For the purposes of the present invention, the term maleic acid derivatives is taken to mean maleic anhydride, maleic acid, maleic monoesters, maleic diesters, fumaric acid, fumaric monoesters and fumaric diesters, the esters being based on the alcohols used for the stripping.

It is also possible to carry out the separation of maleic anhydride from the absorbate phase in a hold tank with attached distillation head, with it being possible for the alcohol to be transported into the tank together with or separately from the absorbate phase. The maleic acid derivatives pass over the distillation head together with the evaporating alcohol.

The countercurrent method is a preferred embodiment of the invention. In a particularly preferred embodiment, further separation stages for retaining the high-boiling, inert absorbent are located between the feed point for the absorbate phase and the column head. Some of the stripping alcohol can be added to the absorbate phase before the feeding into the column. The depleted absorbate phase is obtained at the column bottom, and can be fed to a fresh absorption operation. A high degree of depletion is not necessary, but is desirable. Based on the maleic anhydride content of the head feed, it is generally from 80 to 100%, preferably from 95 to 100%.

The stripping is generally carried out at above 100° C., preferably at from 150 to 300° C., particularly preferably at from 170 to 300° C. The pressure during stripping is generally from 10 mbar to 10 bar, preferably from 100 mbar to 6 bar, particularly preferably from 300 mbar to 5 bar.

During the stripping, maleic anhydride is at least partially esterified by means of the alcohol. A mixture is formed which essentially consists of maleic anhydride, maleic acid, fumaric acid, maleic monoesters, maleic diesters, fumaric monoesters and fumaric diesters. In general a high excess of stripping alcohol favors ester formation. The novel process has the advantage of a small proportion of free maleic or fumaric acid in the head product. In general, the proportion of free acid in the head product, based on the total amount of maleic acid derivatives, is dependent on the amount of water present.

It is furthermore advantageous that the proportion of fumaric esters in the head product is low. The proportion of fumaric monomester and diesters is from 0 to 10% by weight, preferably from 0 to 5% by weight, based on the total amount of maleic acid derivatives.

The present invention furthermore relates to a process for the preparation of maleic esters comprising the following steps:
a) bringing a maleic anhydride-containing gas stream into contact with a liquid absorbent phase comprising at least one inert, high-boiling absorbent having a boiling point which is at least 30° C. higher than that of maleic anhydride,
b) separation of maleic anhydride by stripping with alcohol as stripping agent, where at least some of the maleic anhydride reacts with the alcohol,
c) if desired, further esterification using the alcohol.

Step a) is preferably carried out using a gas stream comprising maleic anhydride-containing reactor offgases from the preparation of maleic anhydride by the oxidation of hydrocarbons.

Separation step b) generally gives a mixture which contains, based on the total amount of maleic esters, from 5 to 95% by weight, preferably from 10 to 90% by weight, of the maleic diester. Separation step b) is preferably followed by a step c) in which the proportion of maleic monoesters and, where appropriate, maleic anhydride or maleic acid or fumaric acid and fumaric monoesters is reduced by further esterification to maleic diesters or fumaric diesters. The esterification is preferably carried out using the stripping alcohol. The esterification of maleic anhydride, maleic acid, maleic monoesters or of carboxylic acids in general is described in EP-A 0 255 399, EP-A 0 454 719, DE-A 5 543 673, DE-A 19 607 953 or in "Organikum", VEB Deutscher Verlag der Wissenschaften, 15th Edition, Berlin, 1977, pp. 498–502. The novel process is preferably used for the preparation of maleic diesters.

The mixture obtained in separation step b) or the mixture obtained by further esterification using the stripping alcohol in step c) of the process described above or the maleic acid derivatives obtained from this mixture by distillation can then be subjected to hydrogenation. Depending on the reaction conditions, 1,4-butanediol, tetrahydrofuran and/or γ-butyrolactone are preferentially obtained.

The present invention also relates to a process for the preparation of at least one compound selected from the group consisting of 1,4-butanediol, γ-butyrolactone and tetrahydrofuran, comprising the following steps:
a) bringing a maleic anhydride-containing gas stream into contact with a liquid absorbent phase comprising at least one inert, high-boiling absorbent having a boiling point which is at least 30° C. higher than that of maleic anhydride,
b) separation of maleic anhydride by stripping with alcohol as stripping agent, where at least some of the maleic anhydride reacts with the alcohol,
c) if desired, further esterification using the alcohol,
d) if desired, separation of the alcohol from the resultant mixture containing the maleic acid derivatives,
e) hydrogenation of the resultant maleic acid derivatives.

Step a) is preferably carried out using a gas stream comprising maleic anhydride-containing reactor offgases from the preparation of maleic anhydride by the oxidation of hydrocarbons.

The maleic acid derivatives obtained in separation step b) can be hydrogenated directly. They may be in the form of a mixture with the stripping alcohol. Advantageous, but not crucial for the success of the hydrogenation, is a high degree of esterification of the resultant maleic acid derivatives. In general, at least 50% by weight, preferably at least 70% by weight, particularly preferably at least 90% by weight, especially preferably at least 95% by weight, in particular at least 97% by weight, of the maleic acid derivatives to be hydrogenated are in the form of maleic diesters. In order to achieve a high degree of esterification, the mixture optained in separation step b) is preferably subjected to a further esterification using the alcohol.

The mixture obtained in separation step b) or by further esterification as in step c) can be subjected to the hydrogenation directly or after separation of the alcohol employed as stripping agent. The hydrogenation is preferably preceded by separation of the alcohol from the resultant mixture as in step d).

The hydrogenation of the resultant maleic acid derivatives can be carried out in the liquid phase or in the gas phase. The hydrogenation can be carried out using homogeneously dissolved catalysts, using suspended catalysts or using fixed-bed catalysts. In general, the hydrogenation catalysts employed contain one or more of the following elements: copper, palladium, platinum, ruthenium, rhenium, cobalt, manganese, nickel, molybdenum and chromium. Such hydrogenation catalysts and the hydrogenations carried out using them are described, for example, in WO 97/43234, EP-A 0 552 463, EP-A 0 724 908, DE-A 2 501 499, BE 851 227, U.S. Pat. No. 4,115,919, EP-A 0 147 219, EP-A 0 417 867, U.S. Pat. No. 5,115,086 and EP-A 0 382 050. During the gas-phase hydrogenation, the temperature is generally from 150 to 250° C. and the pressure is generally from 5 to 100 bar. In the case of hydrogenation in the liquid phase, the temperature is preferably from 100 to 300° C. and the pressure is preferably from 60 to 300 bar.

The alcohol bound in the maleic esters is liberated in the hydrogenation and can be recovered and re-used for stripping.

The novel process is distinguished by the fact that the formation of corrosive acids is substantially supressed. Furthermore, the maleic and fumaric esters formed and the succinic esters formed therefrom by hydrogenation have higher solubility and greater volatility than the free acids, which means that problems caused by deposition on the hydrogenation catalyst are avoided.

The invention is illustrated in greater detail by the examples below.

EXAMPLES

The experiments described below are carried out in an apparatus consisting of a heatable 250 ml distillation flask with still inlet and outlet, a heatable packed column with a length of 50 cm and a width of 3 cm attached thereto, and a distillation attachment with head take-off. The feed for the absorbate, a mixture of dimethyl phthalate as absorbent and maleic anhydride, is located between the upper end of the heatable column and the distillation attachment. Methanol as stripping alcohol is introduced above the still. The feeds and discharges are continuous, and the still level is released in batches. After a running time of 5 hours, samples of the still discharge and the head discharge are taken and analyzed by gas chromatography. The percentages relate to GC area-percent.

Example 1

150 g of dimethyl phthalate are introduced into the still and heated to 220° C. 100 ml/h of methanol are then fed continuously into the still and evaporated. The packed column is heated to 220° C., producing a temperature of about 65° C. at the head of the column. 100 ml/h of a mixture of 80% by weight of dimethyl phthalate and 20% by weight of maleic anhydride are then introduced continuously as head feed, during which the temperature at the column head rises to 140 to 150° C. The still discharge contains 98% to 99% of dimethyl phthalate, about 0.3% of methanol, about 0.3% of maleic anhydride, and about 0.28% of monomethyl and dimethyl maleate. The head discharge contains about 0.8% of maleic anhydride, about 20% of monomethyl maleate, about 14% of dimethyl maleate and about 62% of methanol. Free maleic acid or fumaric acid cannot be detected.

Example 2

The procedure is as described in Example 1, but the head feed comprises 100 ml/h of a mixture of 78.5% by weight of dimethyl phthalate, 19.5% by weight of maleic anhydride and 2% by weight of water, and the still feed comprises 200 ml/h of methanol. The temperature at the column head is about 150° C. The still discharge contains 99% of dimethyl phthalate, about 0.5% of methanol, <0.05% of monomethyl and dimethyl maleate and traces (<0.05%) of maleic anhydride. The head discharge contains <0.05% of maleic anhydride, about 18% of monomethyl maleate, about 1% of dimethyl maleate and about 77% of methanol. The remainder comprises monomethyl fumarate (about 1%) and maleic acid (0.4%) and fumaric acid (<0.05%).

Example 3

The procedure is as described in Example 1, but the head feed comprises 100 ml/h of a mixture of 79.7% by weight of dimethyl phthalate, 19.9% by weight of maleic anhydride and 0.4% by weight of water, and the still feed comprises 100 ml/h of methanol. The temperature at the column head is about 150° C. The still discharge contains about 99.2% of dimethyl phthalate, about 0.3% of methanol, <0.05% of monomethyl and dimethyl maleate and <0.05% of maleic anhydride. The head discharge contains <0.05% of maleic anhydride, about 14% of monomethyl maleate, about 11% of dimethyl maleate, about 2% of monomethyl fumarate and about 72% of methanol. Free maleic acid (about 0.5%) and fumaric acid (<0.05%) were only present in small amounts.

We claim:

1. A process for the separation of maleic anhydride from a maleic anhydride-containing gas stream in which
    a) the maleic anhydride-containing gas stream is brought into contact with a liquid absorbent phase containing at least one high-boiling, inert absorbent for maleic anhydride, and
    b) maleic anhydride is separated from the resultant liquid absorbate phase by vapor stripping, wherein the stripping agent used is an alcohol, at least some of the maleic anhydride reacting with the alcohol.

2. A process as claimed in claim 1, wherein the high-boiling, inert absorbent has a boiling point which is at least 30° C. higher than that of maleic anhydride.

3. A process as claimed in claim 1, wherein the alcohol employed as a stripping agent is selected from the group consisting of methanol, ethanol and n-butanol.

4. A process as claimed in claim 1, wherein the gas stream employed is a maleic anhydride-containing reactor offgas from the preparation of maleic anhydride by the oxidation of hydrocarbons.

5. A process as claimed in claim 1, where the process is carried out using maleic anhydride-containing reactor off-gases from the preparation of maleic anhydride by the oxidation of hydrocarbons.

6. A process as claimed in claim 1, for the preparation of diesters of maleic acid.

7. A process as claimed in claim 2, comprising the additional steps:
    c) further esterification of the resultant mixture using the alcohol, wherein esters of maleic acid are obtained.

8. A process as claimed in claim 2 comprising the following additional steps:
    c) optionally, further esterification using the alcohol,
    d) optionally, separation of the alcohol from the resultant mixture containing maleic acid derivatives,
    e) hydrogenation of the resultant maleic acid derivatives wherein at least one compound selected from the group consisting of 1,4-butanediol, γ-butyrolactone and tetrahydrofuran is obtained.

* * * * *